United States Patent [19]

Nissen et al.

[11] Patent Number: 4,742,008

[45] Date of Patent: May 3, 1988

[54] PREPARATION OF THE ENZYME BETA-GLUCANASE BY FERMENTATION OF FUNGI

[75] Inventors: Bernt Nissen, Rykkin; Jon Hovland, Porsgrunn, both of Norway

[73] Assignee: Norsk Hydro a.s., Oslo, Norway

[21] Appl. No.: 881,351

[22] PCT Filed: Jun. 20, 1985

[86] PCT No.: PCT/NO85/00036

§ 371 Date: Jun. 4, 1986

§ 102(e) Date: Jun. 4, 1986

[87] PCT Pub. No.: WO86/02946

PCT Pub. Date: May 22, 1986

[30] Foreign Application Priority Data

Nov. 8, 1984 [NO] Norway ................................ 844.455

[51] Int. Cl.$^4$ ........................... C12N 9/24; C12R 1/785
[52] U.S. Cl. ........................................ 435/200; 435/931
[58] Field of Search ................................ 435/200, 931

[56] References Cited

U.S. PATENT DOCUMENTS

| | | | |
|---|---|---|---|
| 3,880,742 | 4/1975 | James et al. | 435/200 |
| 4,275,163 | 6/1981 | Gallo | 435/209 |
| 4,399,221 | 8/1983 | Schneider et al. | 435/193 |
| 4,588,690 | 5/1986 | Nissen et al. | 435/200 |

*Primary Examiner*—Lionel M. Shapiro
*Attorney, Agent, or Firm*—Wenderoth, Lind & Ponack

[57] ABSTRACT

β-glucanase is produced under submerged, aerobic and thermophilic conditions, by cultivating the microorganism *Rhizomucor pusillus* (Lindt) Schipper, preferably the strain CBS 551.82. Fermentation is carried out using a fed batch method, where a carbon source such as barley meal is first introduced, and when this is consumed, a sugar compound, preferably lactose, is added, whereupon the fermentation continues until the carbon source is completely or partially consumed.

4 Claims, 1 Drawing Sheet

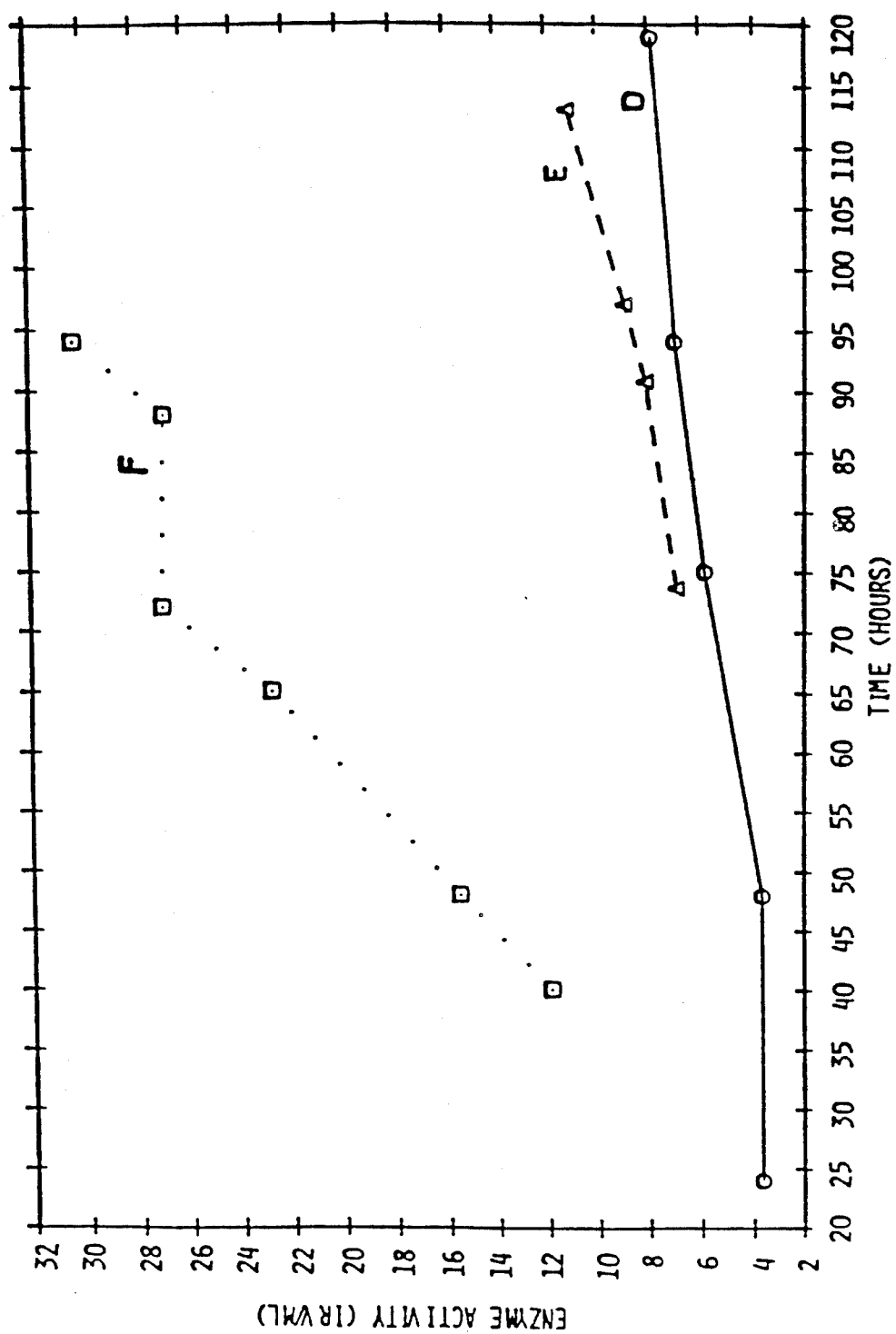

PREPARATION OF THE ENZYME BETA-GLUCANASE BY FERMENTATION OF FUNGI

This invention concerns a procedure for the production of β-glucanase through the cultivation of a microorganism in a nutrient medium under optimal conditions.

We refer to Norwegian patent application No. 82 4321 concerning the use of microorganisms of the species *Rhizomucor pusillus* (Lindt) Schipper as being suitable for the above process, as well as an isolated and registered strain of the stated microorganism CBS 551.82 (Centraalbureau voor Schimmelcultures, Nederland) being particularly suitable for the production of the enzyme β-glucanase.

The purpose of this invention is to optimize fermentation such that maximum enzyme yield within the shortest possible time is achieved, yet under the same conditions as otherwise stated in Norwegian patent application No. 82 4321, that is, to conduct fermentation under thermophilic conditions and wherein the microorganism is thermostable under the said conditions. In addition to the significance that the microorganism (*Rhizomucor pusillus* (Lindt) Schipper CBS 551.87) has for a positive result, it should also be mentioned that the composition of the nutrient medium, the air delivery rate and apparatus design are all important factors for the achievement of optimal conditions for fermentation.

Vegetable meal and starchy substances, as well as sugars, are commonly used as carbon sources for fermentation purposes. However, not all carbon sources have proven to be suitable for this purpose. The cause of this has not been definitely ascertained, but different factors appear to have an influence on the transformation of sugar into energy. If the source of carbon is to be used as an energy source, the following factors at least seem to be of significance: the solubility of the source of carbon and its ability to be taken up through the system of cell wall and membrane.

It now appears, astonishingly enough, that if we apply a two-stage fermentation with lactose as the source of carbon in a fermentation process using the previously mentioned microorganisms, then the enzyme yield increases several times when all conditions are met.

Under batch conditions, the fermentation exhibits the traditional growth pattern with a lag phase, exponential growth and a stationary phase where enzyme production is greatest in the stationary phase. It is important that the fermentation is carried out under aerobic conditions. This places great demands on the stirring machinery and on the stirring speed. If the stirring is too vigorous, then the fungal hyphae (microorganisms) are disintegrated, and if it is too weak, oxygen is not distributed sufficiently in the fermentor. Both factors reduce enzyme formation. Furthermore, too vigorous stirring combined with a low oxygen content promotes a threadlike structure in the fungal hyphae, whereas a more pellet-like structure is desired.

For a better understanding of the invention we refer to Examples 1-8.

EXAMPLE 1

(a) 300 ml of an inoculum of *Rhizomucor pusillus* (Lindt) Schipper CBS 551.82 was mixed in a 14 l fermentor with 10 l of a salt medium of the following composition:

$KH_2PO_4$ : 2.00 g/l
$MgSO_4 . 7 H_2O$: 1.75 g/l
$CaCl_2$ : 0.20 g/l
Trace mineral solution: 2.5 ml/l
Water: 1.0 l The trace mineral solution has the following composition:

$CuSo_4 . 5 H_2O$: 1.0 g/l
$FeSO_4 . 7 H_2O$: 15.0 g/l
$ZnSO_4 . 7 H_2O$: 6.2 g/l
$MnSO_4 . H_2O$: 1.5 g/l
Conc. $H_2SO_4$: 1.5 ml/l The fermentation was carried out with 40 g/l barley meal as the carbon source and 13.4 g/l $NH_4Cl$ as the nitrogen source. Berol 374 from Berol Kemi AB, Sweden, was used as an anti-foaming agent. The stirring rate was 600 rpm, the temperature 40° C. and pH 4.5. The fermentor's air delivery was set to 3 vvm, that is, 30 l air/min. (1 vvm is 1 l air per 1 nutrient medium per min.). Fermentation time was 45 hours. (b) An inoculum of the above mentioned 10 l nutrient medium was mixed in a 300 l fermentor with 200 l of the salt medium described above.

Fermentation was carried out according to the batch method, with a mixture of 40 g/l barley meal and 13.4 g/l $NH_4Cl$ at pH 4.5 and a temperature of 40° C., and a stirring rate of 410 rpm. The fermentor's air delivery rate was 0.2 vvm, or 40 l air/min. The enzyme activity was 2.5 EU/ml after 79 hours and 2.7 EU/ml after 92 hours according to Dygert's method (Analytical Biochemistry, vol. 13 (1965) pp. 367–374).

EXAMPLE 2

An inoculum from a 14 l fermentor holding the conditions described in Example 1 was put into a 300 l fermentor in a quantity of 9 l and cultivated using the batch method with 20, 30, 40 and 50 g/l barley meal and fermented as in Example 1b.

As the following table shows, enzyme activity changed with changing barley meal concentrations:

20 g barley meal/l: 2.00 IRV/ml
30 g barley meal/l: 6.50 IRV/ml
40 g barley meal/l: 7.50 IRV/ml
50 g barley meal/l: 1.50 IRV/ml IRV is the "Increase in Reciprocal Viscosity". This can be compraed with enzyme activity (EU/ml) as measured by Dygert's method using the following formula:

$$IRV/ml = EU/ml \times 2.5$$

Otherwise we refer to J. Inst. Brewing, Vol. 85 (1979), pp. 92–94, where the capillary-viscosimetric method, giving the result in terms of IRV units, is discussed.

EXAMPLE 3

An inoculum from a 14 l fermentor holding the cultivating conditions described in Example 1a, was put into a 300 l fermentor in a quantity of 9 l and cultivated according to the fed batch method, using 15 g/l barley meal in the beginning stage and $NH_4Cl$ in a concentration of 1.38 g/l. When the barley meal was consumed, glucose was added at a feed rate of 1.5 g/min. with a total C-source consumption of 40 g/l. The pH was adjusted to 4.5 using an equivalent mixture of $NH_3$ and NH₄Cl, and the fermentation was carried out under constant temperature conditions at 40° C. The stirring rate was 410 rpm and the fermentor's air delivery rate was 40 l/min. Berol 374 was used as a foaming inhibitor. Fermenting time was 110 h. Enzyme activity according to the capillary-viscosimetric method was 11.1 IRV/ml.

EXAMPLE 4

An inoculum from a 14 l fermentor holding the conditions described in Example 1b was put into a 300 l fermentor in a quantity of 9 l and cultivated according to the fed batch method, as described in Example 3, with the exception that 25 g lactose/l was used instead of glucose. Fermenting time: 95 hours. Enzyme activity according to the capillary-viscosimetric method was 30.4 IRV/ml.

EXAMPLE 5

The procedure was the same as in Example 4, except that the lactose quantity was increased to 35 g lactose/l. Fermenting time: 95 hours. Enzyme activity according to the capillary-viscosimetric method was 38.0 IRV/ml.

EXAMPLE 6

The procedure was the same as in Example 4, except that sucrose was used as the carbon source. Enzyme activity was measured as 2.6 IRV/ml.

EXAMPLE 7

Lactose only was used as a carbon source for the fermentation. The fermentation was otherwise carried out as described in Example 1. Enzyme activity was measured as 8.2 IRV/ml.

EXAMPLE 8

The procecure was the same as in Example 4, but raffinose was used as the carbon source. Enzyme activity was measured as 6.7 IRV/ml.

In the examples that have been discussed, both a simple "batch" method and a "fed batch" method, as described in Examples 1,2 and 3, 4, 5, 6, 7 and 8 respectively, have been used. The batch method usually yields a fungal hyphae with a threadlike structure, which among other things impedes filtering. The fed batch method, however, produces the fungal hyphae in fine-grained, homogeneous pellets, which is preferable for reasons concerning process technology.

The cause of this favourable operational result seems to rest with the fact that in the fed batch method, the fungal hyphae is limited by the carbohydrate supply rather than by the oxygen supply, as with the simple batch method.

Otherwise we refer to FIG. 1 which shows the increase in enzyme activity in relation to fermenting time.

Curves D, E and F show the increase in enzyme activity when fermentation is carried out as in Examples 1, 3 and 4.

We claim:

1. A process for producing β-glucanase under submerged, aerobic and thermophilic conditions, which comprises cultivating in a nutrient medium a fungal strain of *Rhizomucor pusillus* (Lindt) Schipper, wherein an inoculum of said strain is introduced into a fermentor containing a nutrient medium and fermentation occurs according to a fed batch method, where a starchy vegetable meal is added first as a source of carbon, and when said starchy vegetable meal is completely or partially consumed, a sugar compound selected from the group consisting of lactose, glucose, sucrose and raffinose is then introduced as a source of carbon, whereupon the fermentation continues until the carbon source is completely or partially consumed.

2. The process according to claim 1, wherein the fungal strain is *Rhizomucor pusillus* (Lindt) Schipper CBS 551.82.

3. The process according to claim 1, wherein the starchy vegetable meal is barley meal.

4. The process according to claim 1, wherein the sugar compound is lactose.

* * * * *